US011820338B2

(12) United States Patent
Schmalenberg et al.

(10) Patent No.: US 11,820,338 B2
(45) Date of Patent: Nov. 21, 2023

(54) AUTONOMOUS VEHICLE CLEANING AND FEEDBACK SYSTEM USING ADJUSTABLE GROUND TRUTH

(71) Applicant: TOYOTA MOTOR ENGINEERING & MANUFACTURING NORTH AMERICA, INC., Plano, TX (US)

(72) Inventors: Paul D. Schmalenberg, Pittsburgh, PA (US); Sean P. Rodrigues, Ann Arbor, MI (US); Atsushi Iwai, Pittsburgh, PA (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 278 days.

(21) Appl. No.: 17/172,436

(22) Filed: Feb. 10, 2021

(65) Prior Publication Data

US 2022/0250589 A1  Aug. 11, 2022

(51) Int. Cl.
*B60S 1/64* (2006.01)
*B60Q 3/80* (2017.01)

(52) U.S. Cl.
CPC . *B60S 1/64* (2013.01); *B60Q 3/80* (2017.02)

(58) Field of Classification Search
CPC ................ B60S 1/64; B60Q 3/80; B60N 2/06
See application file for complete search history.

(56) References Cited

U.S. PATENT DOCUMENTS

| | | | |
|---|---|---|---|
| 9,550,006 B2 | 1/2017 | Boodaghians et al. | |
| 10,290,158 B2 | 5/2019 | Jales Costa et al. | |
| 10,304,165 B2 | 5/2019 | Tokatyan | |
| 10,427,650 B2 | 10/2019 | Salter et al. | |
| 10,509,974 B2 | 12/2019 | Tokatyan | |
| 10,611,269 B1* | 4/2020 | Larner | B60N 2/4207 |
| 2016/0280097 A1* | 9/2016 | Hotary | B60N 2/0244 |
| 2017/0115826 A1 | 4/2017 | Pryor | |
| 2017/0210352 A1* | 7/2017 | Stauffer | B60Q 9/00 |
| 2018/0330475 A1* | 11/2018 | Tokatyan | G06K 9/6267 |
| 2019/0091738 A1* | 3/2019 | Chen | B60H 1/00742 |
| 2019/0210518 A1* | 7/2019 | Michalakis | B60K 35/00 |
| 2020/0061223 A1* | 2/2020 | Hallack | B60N 2/002 |

(Continued)

FOREIGN PATENT DOCUMENTS

| | | |
|---|---|---|
| DE | 102012006972 A1 | 10/2013 |
| KR | 101640093 B1 | 7/2016 |
| WO | 2020170680 A1 | 8/2020 |

*Primary Examiner* — Alexander H Taningco
*Assistant Examiner* — Pedro C Fernandez
(74) *Attorney, Agent, or Firm* — HAYNES AND BOONE, LLP

(57) ABSTRACT

A vehicle includes a cleanable surface disposed within its interior. The vehicle also includes a processor, a light source able to illuminate the surface, and a sensor configured to capture an image of the surface while the surface is illuminated by the light source. The vehicle also includes a passenger survey system for receiving input from a passenger regarding cleanliness of the surface. The processor is configured to adjust a detection threshold based on the input, and to detect foreign material on the surface based on the detection threshold and a comparison between the captured image and a stored image. After detecting the foreign material on the surface, the processor indicates that the vehicle needs to be cleaned, and may initiate an automatic cleaning procedure.

20 Claims, 7 Drawing Sheets

(56) References Cited

U.S. PATENT DOCUMENTS

| | | | |
|---|---|---|---|
| 2021/0208590 A1* | 7/2021 | Cho | G06Q 30/0185 |
| 2021/0322613 A1* | 10/2021 | Lacaze | G06N 20/00 |
| 2022/0118130 A1* | 4/2022 | Mayo | B60S 1/64 |

* cited by examiner

AUTONOMOUS VEHICLE CLEANING AND FEEDBACK SYSTEM USING ADJUSTABLE GROUND TRUTH

TECHNICAL FIELD

The subject matter described herein relates to an autonomous cleaning system for vehicle interiors that incorporates passenger feedback and adjustable ground truth. This autonomous vehicle cleaning system has particular, but not exclusive, utility for maintaining cleanliness of Mobility-as-a-Service (MaaS) cars, vans, and trucks.

BACKGROUND

Ultraviolet (UV) light emission is a known technology used to clean the inside surfaces of a vehicle by killing bacteria/viruses, breaking down organic molecules, and bleaching. Although UV lights may be used to clean surfaces within a vehicle. UV lights do not always reach hard-to-reach spaces or clean deep stains. Passengers may enter a vehicle and notice that there are some areas of the vehicle that aren't actually clean, even though UV lights had been activated prior to their entering. In some cases, a dirty vehicle may present health hazards, as with influenza, COVID, and other potentially deadly pathogens. UV light can also be hazardous to human health. Care must be taken to ensure humans and animals are not in the vehicle when UV cleaning lights are activated.

In Mobility-as-a-Service (MaaS) vehicles such as taxis, autonomous taxis, e-palettes, etc. it can be difficult to clean the vehicle between rides, with passengers coming and going. For autonomous MaaS vehicles to get completely clean without the help of an available driver, they need to be sent to a cleaning service facility, which must then inspect and clean the vehicle. Furthermore, as a vehicle ages, its interior can accumulate scratches, scrapes, dents, and other wear defects that could be mistaken for dirt, stains, or other foreign matter, but cannot be cleaned away in the same manner as dirt or debris.

It should be understood that current vehicle cleaning systems and methods have numerous drawbacks, including but not limited to frequent service visits, passenger health hazards, insufficient cleaning in hard-to-reach areas, and lack of interactivity. Accordingly, a need exists for improved vehicle cleaning systems and methods that address the foregoing and other concerns.

The information included in this Background section of the specification, including any references cited herein and any description or discussion thereof, is included for technical reference purposes only and is not to be regarded as subject matter by which the scope of the disclosure is to be bound.

SUMMARY

Disclosed is an autonomous vehicle cleaning system with adjustable ground truth, that detects and addresses foreign material in a vehicle interior. This autonomous vehicle cleaning system may employ light sources, 2D or 3D sensors, window dimming, autonomous driving, UV sterilization, or cleaning fluids. The autonomous vehicle cleaning system may for example be activated autonomously when all occupants have left the vehicle, and may detect the locations of stains, spills, dirt, trash, debris, and other foreign material, and may either attempt to clean the surfaces on which they occur, or may autonomously deliver the vehicle to a service location for cleaning. The system permits passengers who are exiting the vehicle to take a survey indicating whether or not they believe the vehicle is clean, and this feedback is then used to adjust detection thresholds for identifying areas of the vehicle that need cleaning. Detection may involve automatically moving seats and imaging the vehicle interior using alternate light sources. Cleaning may involve UV sterilization or the dispensing of cleaning fluids.

The autonomous vehicle cleaning system disclosed herein has particular, but not exclusive, utility cleaning MaaS vehicles in between passengers. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a vehicle that includes an interior and an exterior. The vehicle also includes a surface disposed within the interior, a processor; a light source configured to illuminate the surface; a sensor configured to, under control of the processor, capture an image of the surface while the surface is illuminated by the light source; and a stored image of the surface; a detection threshold; and a passenger survey system configured to receive an input from a passenger regarding cleanliness of the surface, where the processor is configured to adjust the detection threshold based on the input; where the processor is configured to detect foreign material on the surface based on the detection threshold and a comparison between the captured image and the stored image, and where the processor is configured to, after detecting the foreign material on the surface, indicate that the vehicle needs to be cleaned. Other embodiments of this aspect include corresponding computer systems, apparatus, and computer programs recorded on one or more computer storage devices, each configured to perform the actions of the methods.

Implementations may include one or more of the following features. In some embodiments, the passenger survey system is disposed within the interior of the vehicle, and the vehicle further includes a cleaning element configured to, when activated by the processor indicating that the vehicle needs to be cleaned, clean the surface. In some embodiments, the passenger survey system includes a touchscreen, a voice interface, a gesture interface, or a housing including electromechanical buttons. In some embodiments, the processor is configured to activate the cleaning element for: a fixed period of time, a period of time based on the input, or a period of time based on a property of the detected foreign material. In some embodiments, the cleaning element is a UV lamp or a cleaning fluid delivery system. In some embodiments, the vehicle further includes a movable seat and a seat control system configured to, under control of the processor, move the movable seat such that the surface is exposed. In some embodiments, the vehicle further included an external light control system configured to adjust an amount of external light entering the interior of the vehicle prior to activation of the light source. In some embodiments, the external light control system includes automatic curtains, automatic shades, automatic louvres, automatic visors, electrochromic elements, an automatic garage door controller, or an autonomous driving system configured to drive the vehicle to a location with a desirable lighting condition. In some embodiments, the passenger survey system is further configured to receive a second input from the passenger regarding a wear defect of the surface, and the processor is configured, via the light source and sensor, to update the stored image of the surface to include the wear defect. In some embodiments, the light source and the sensor include a lidar, the light source includes an ultraviolet (UV) light source, and the sensor includes a UV, visible light, or infrared (IR) sensor, the light source includes a visible light source, and the sensor includes a visible light camera; or the light source includes an infrared light source, and the sensor includes an infrared sensor. Implementations of the described techniques may include hardware, a method or process, or computer software on a computer-accessible medium.

One general aspect includes a method for cleaning an interior surface of a vehicle. In a vehicle including an interior and an exterior, the method includes providing a surface disposed within the interior; under control of a processor; illuminating the surface with a light source; capturing a baseline image of the surface with a sensor, while the surface is illuminated by the light source; storing the baseline image; defining a detection threshold; with a passenger survey system, receiving an input from a passenger regarding cleanliness of the surface, adjusting the detection threshold based on the input; capturing a current image of the surface with a sensor, while the surface is illuminated by the light source; detecting foreign material on the surface based on the detection threshold and a comparison between the current image and the stored image; and after detecting the foreign material on the surface, cleaning the surface by activating a cleaning element. Other embodiments of this aspect include corresponding computer systems, apparatus, and computer programs recorded on one or more computer storage devices, each configured to perform the actions of the methods.

Implementations may include one or more of the following features. In some embodiments, the passenger survey system is disposed within the interior of the vehicle, and the passenger survey system includes a touchscreen, a voice interface, a gesture interface, or a housing including electromechanical buttons. In some embodiments, the method further includes: under control of the processor, moving a movable seat such that the surface is exposed. In some embodiments, the method further included adjusting an amount of external light entering the interior of the vehicle prior to activation of the light source. In some embodiments, adjusting the amount of external light entering the interior includes activating automatic curtains, automatic shades, automatic louvres, automatic visors, electrochromic elements, an automatic garage door controller, or an autonomous driving system configured to drive the vehicle to a location with a desirable lighting condition. In some embodiments, the method further includes: under control of the processor; with the passenger survey system, receiving a second input from the passenger regarding a wear defect of the surface; and with the light source and sensor, updating the stored image of the surface to include the wear defect. In some embodiments, activating the cleaning element includes turning on the cleaning element for: a fixed period of time, a period of time based on the input, or a period of time based on a property of the detected foreign material. In some embodiments, the cleaning element is a UV lamp or a cleaning fluid delivery system. In some embodiments, the light source and the sensor include a lidar, the light source includes an ultraviolet (UV) light source, and the sensor includes a UV, visible light, or infrared (IR) sensor, the light source includes a visible light source, and the sensor includes a visible light camera; or the light source includes an infrared light source, and the sensor includes an infrared sensor. Implementations of the described techniques may include hardware, a method or process, or computer software on a computer-accessible medium.

One general aspect includes a system for cleaning a surface of an interior of a vehicle. The system includes the vehicle, where the vehicle includes an interior and an exterior. The system also includes a surface disposed within the interior; a processor; a light source configured to illuminate the surface; a sensor configured to, under control of the processor, capture an image of the surface while the surface is illuminated by the light source; a stored image of the surface; a cleaning element configured to, when activated by the processor, clean the surface, a detection threshold; a movable seat; a seat control system configured to, under control of the processor, move the movable seat such that the surface is exposed; an external light control system configured to, under control of the processor, adjust an amount of external light entering the interior of the vehicle prior to activation of the light source; and a passenger survey system disposed within the interior of the vehicle and configured to receive an input from a passenger regarding cleanliness of the surface, where the processor is configured to adjust the detection threshold based on the input. The processor is configured to detect foreign material on the surface based on the detection threshold and a comparison between the captured image and the stored image. The processor is further configured to, after detecting the foreign material on the surface, activate the cleaning element. Other embodiments of this aspect include corresponding computer systems, apparatus, and computer programs recorded on one or more computer storage devices, each configured to perform the actions of the methods.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the autonomous vehicle cleaning system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
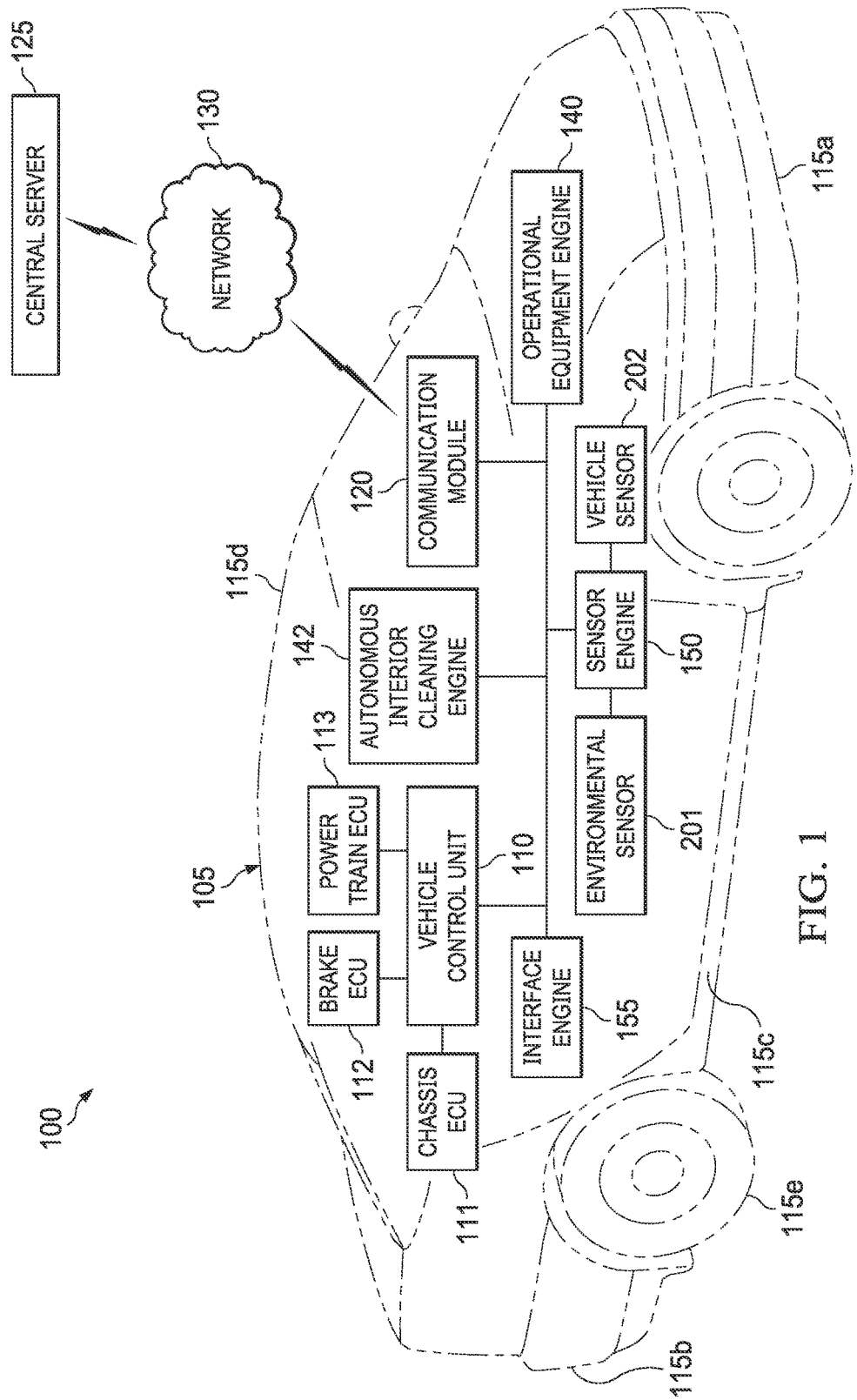
FIG. 1 is a diagrammatic illustration of an autonomous vehicle cleaning system with adjustable ground truth, in accordance with at least one embodiment of the present disclosure.

Disclosed is an autonomous vehicle cleaning system with adjustable ground truth, that detects and addresses foreign material in a vehicle interior. The operation of the system begins by having passengers who are exiting the vehicle take a survey in the form of pressing buttons or operating other controls within the vehicle, or on an app, to convey whether or not they believe the vehicle is clean. Passengers may have the option to point out specific areas on the vehicle that need to be cleaned (e.g., by gesturing at them or describing their locations). After the system has analyzed the survey result, the system may compare the results with before-and-after sensor images. The cleaning process then begins once the system determines (e.g., by using 3D sensors, cameras, etc.) that there are no human or animal occupants in the vehicle. Once it is determined that no occupants are within the vehicle, the UV light is turned on to sanitize the vehicle. The UV light is then turned off either after a predetermined, foxed period of time or a calculated period time for cleaning based on the properties (e.g., size, severity, quantity) of the detected foreign material (e.g., how dirty the vehicle interior is). An alternate light source is then turned on and a scene of the vehicle interior is recorded. With the alternate light source, sensors can detect stains that might not be apparent with a 3D LIDAR sensor or visible light camera under a white light source. Next, a 3D profile of the vehicle cabin area may be recorded using a 3D sensor.

Both recordings are compared to the two established ground truths (e.g., stored images of the clean vehicle interior captured with the same sensors and light sources). If either of the recordings do not correspond to their respective ground truths, the system will return to the step of cleaning with the UV light. Finally, when the next passengers exit the vehicle, they will also be asked to take the survey, and the system will again compare the passenger feedback with the sensor data. The ground truth parameters (e.g., one or more cleanliness thresholds) are adjusted accordingly, if needed. The survey may also ask the user to rate the condition of the vehicle due to wear and tear, or to point out where in the vehicle there are any noticeable wear defects (e.g., cracks in seats, worn carpet or upholstery, etc.). The system may then adjust the ground truth (e.g., by capturing and storing new baseline images of the clean vehicle) so that such wear is not mistaken for dirt or debris. Instead of or in addition to UV lights, the vehicle may use aerosol sprays to clean the vehicle's interior surfaces.

The present disclosure advantageously provides a feedback interface display or feedback station inside the vehicle, using the on-board computer and communication systems and network capabilities to relay information regarding the comments, ratings, and complaints from passengers relating to vehicle cleanliness, and to trigger on-board cleaning, disinfectant, and/or deodorizing cycles immediately after passengers have provided the feedback and exited the vehicle. Thus, stains and spills may be promptly addressed. Such passenger-provided data may also flag vehicle components or other vehicle areas to be further cleaned or inspected off-site or when the vehicle is returned to a service area.

The autonomous vehicle cleaning system may employ UV, visible light, and infrared sensors, along with appropriate light sources, as well as 3D sensors, window dimming, autonomous driving, UV sterilization, or the dispensing of cleaning fluids. The autonomous vehicle cleaning system may for example be activated autonomously when all occupants have left the vehicle, and may detect the locations of stains, spills, dirt, trash, debris, and other foreign material, and may either attempt to clean them or may deliver the vehicle to a service location for cleaning. In some embodiments, the autonomous vehicle cleaning system controls dimmable windows and or moves the vehicle to a new location in order to adjust interior lighting conditions for optimal detection.

The present disclosure represents an improvement over the existing art, because it provides a means to detect and clean foreign matter, including adjusting the vehicle seats so that the sensors and cleaning methods can reach all areas that future passengers are likely to encounter. Input from passengers is used to augment sensors in determining whether the vehicle needs to be cleaned. To ensure an appropriate level of external light entering the vehicle, the vehicle may sanitize only at certain times of day, may travel to areas with appropriate lighting (e.g., a parking garage), or may activate sun blocking systems (e.g., roller shades or curtains, sun visors, sunroof panels, and even controllable tinted windows).

The vehicle's ground truth is established by passenger feedback, and by capturing images (e.g., 3D images) of the vehicle's interior with one or more light sources and imaging sensors. The first recording may for example be of the vehicle interior with all of the seats in an upright position to capture most of the floor between the seats. The second recording may be of the vehicle interior with all of the seats in full recline position to capture the entire seating surface, or a stowed position where the entire cargo area may be captured by the imaging system for detecting debris and establishing a baseline ground troth that may be updated periodically.

During cleaning operations, the system may control exterior light entering the vehicle, either by dimming the windows or by commanding the vehicle to drive autonomously to a location with desirable lighting conditions. Next, foldable vehicle seats are moved to a desired configuration for imaging and/or cleaning. Vehicle seats are then pulled back into a new position to repeat the cleaning process, and new images are recorded.

Although the present disclosure provides a system to allow a self-driving or semi-autonomous vehicle to seek an ideal or optimal location (or provide instructions or a warning to a human driver to do so), the improved lighting condition need only improve the conditions, for example, by moving away from the interfering sunlight or street lamp to where it becomes sufficient to monitor the vehicle interior for spills and stains. Alternatively, where light is dim lit and lighting conditions are poor, the vehicle may also drive to a more optimal location or turn on exterior lights or open a closed garage to create a better lighting environment.

With the autonomous vehicle cleaning system of the present disclosure, a self-driving vehicle is able to drive to a new location or re-position the vehicle to a different orientation when light interferes with the stain detection means (e.g., a camera or other imaging sensor) using the alternate light source (e.g., 1550 nm near-IR light). For example, where the light interferes with the imaging device's capabilities to detect stains, spills, dirt, or the like, the present invention provides a detection means for identifying when exterior lighting may interfere with the imaging device (or where lighting is poor or inadequate), whereupon the vehicle will move itself to seek optimal lighting conditions, for instance, by driving to a shaded area, into an indoor garage, or simply by turning the orientation of the vehicle to keep the exterior light from interfering with the receptors, lens, imaging capabilities or performance, and/or quality of the emitting rays that could compromise the system's ability to sense, receive or detect interior soils, stains and debris.

The present disclosure aids substantially in keeping vehicles (e.g., MaaS vehicles) clean, by improving detection and remediation of foreign material in between passenger pickups. Implemented as a system that integrates with existing vehicle components and subsystems, the autonomous vehicle cleaning system disclosed herein provides a practical means to detect foreign material and either clean it directly or else direct service personnel to clean it. This improved detection and cleaning process transforms potentially dirty vehicles into clean vehicles that are safer and more comfortable for passengers, without the normally routine need to rely on service technicians to identify soiled areas within the vehicle. This unconventional approach improves the functioning of the MaaS vehicle, by increasing in-service time and passenger comfort. A control process of the autonomous vehicle cleaning system may perform certain specific operations in response to different sensor inputs.

These descriptions are provided for exemplary purposes only, and should not be considered to limit the scope of the autonomous vehicle cleaning system. Certain features may be added, removed, or modified without departing from the spirit of the claimed subject matter. For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic illustration of an autonomous vehicle cleaning system with adjustable ground truth, in accordance with at least one embodiment of the present disclosure. In an example, the autonomous vehicle cleaning system is referred to by the reference numeral 100 and includes a vehicle 105, such as an automobile, and a vehicle control unit 110 located on the vehicle 105. The vehicle 105 may include a front portion 115a (including a front bumper), a rear portion 15b (including a rear bumper), a right side portion 115c (including a right front quarter panel, a right front door, a right rear door, and a right rear quarter panel), a left side portion 115d (including a left front quarter panel, a left front door, a left rear door, and a left rear quarter panel), and wheels 115e. A communication module 120 may be operably coupled to, and adapted to be in communication with, the vehicle control unit 110. The communication module 120 may in some cases be adapted to communicate wirelessly with a central server 125 via a network 130 (e.g., a 3G network, a 4G network, a 5G network, a Wi-Fi network, or the like). The central server 125 may provide information and services including but not limited to include location, mapping, route or path, and topography information.

An operational equipment engine 140 is operably coupled to, and adapted to be in communication with, the vehicle control unit 110. A sensor engine 150 is operably coupled to, and adapted to be in communication with, the vehicle control unit 110. The sensor engine 150 is adapted to monitor various components of, for example, the operational equipment engine 140. An interface engine 155 is operably coupled to, and adapted to be in communication with, the vehicle control unit 110. In addition to, or instead of, being operably coupled to, and adapted to be in communication with, the vehicle control unit 110, the communication module 120, the operational equipment engine 140, the sensor engine 150, and/or the interface engine 155 may be operably coupled to, and adapted to be in communication with, another of the components via wired or wireless communication (e.g., via an in-vehicle network). In some examples, the vehicle control unit 110 is adapted to communicate with the communication module 120, the operational equipment engine 140, the sensor engine 150, or the interface engine 155 to at least partially control the interaction of data with and between the various components of the autonomous vehicle cleaning system 100.

The term "engine" is meant herein to refer to an agent, instrument, or combination of either, or both, agents and instruments that may be associated to serve a purpose or accomplish a task-agents and instruments may include sensors, actuators, switches, relays, power plants, system wiring, computers, components of computers, programmable logic devices, microprocessors, software, software routines, software modules, communication equipment, networks, network services, and/or other elements and their equivalents that contribute to the purpose or task to be accomplished by the engine. Accordingly, some of the engines may be software modules or routines, while others of the engines may be hardware and/or equipment elements in communication with any or all of the vehicle control unit 110, the communication module 120, the network 130, or a central server 125.

In this example, the vehicle 105 also includes a chassis electronic control unit (ECU) 111 which controls elements of the vehicle's suspension system, a brake ECU 112 which controls the braking system or elements thereof, a power train ECU 113 (variously known as an engine ECU, power plant ECU, motor ECU, or transmission ECU) that controls elements of the motor and drivetrain. The system also includes one or more environmental sensors 201, one or more vehicle sensors 202, and an autonomous interior cleaning engine 142, the operation of which will be described below.

A reader of ordinary skill in the art will understand that other components or arrangements of components may be found in a vehicle 105, and that the same general principles apply to electric vehicles, internal combustion vehicles, and hybrid vehicles. For example, a power train ECU 113 may control both motor and transmission components. Alternatively, a separate motor ECU and transmission ECU may exist, or some functions of a motor ECU or transmission ECU may be performed by the VCU 110.

Before continuing, it should be noted that the examples described above are provided for purposes of illustration, and are not intended to be limiting. Other devices and/or device configurations may be utilized to carry out the operations described herein.

Figure 2:
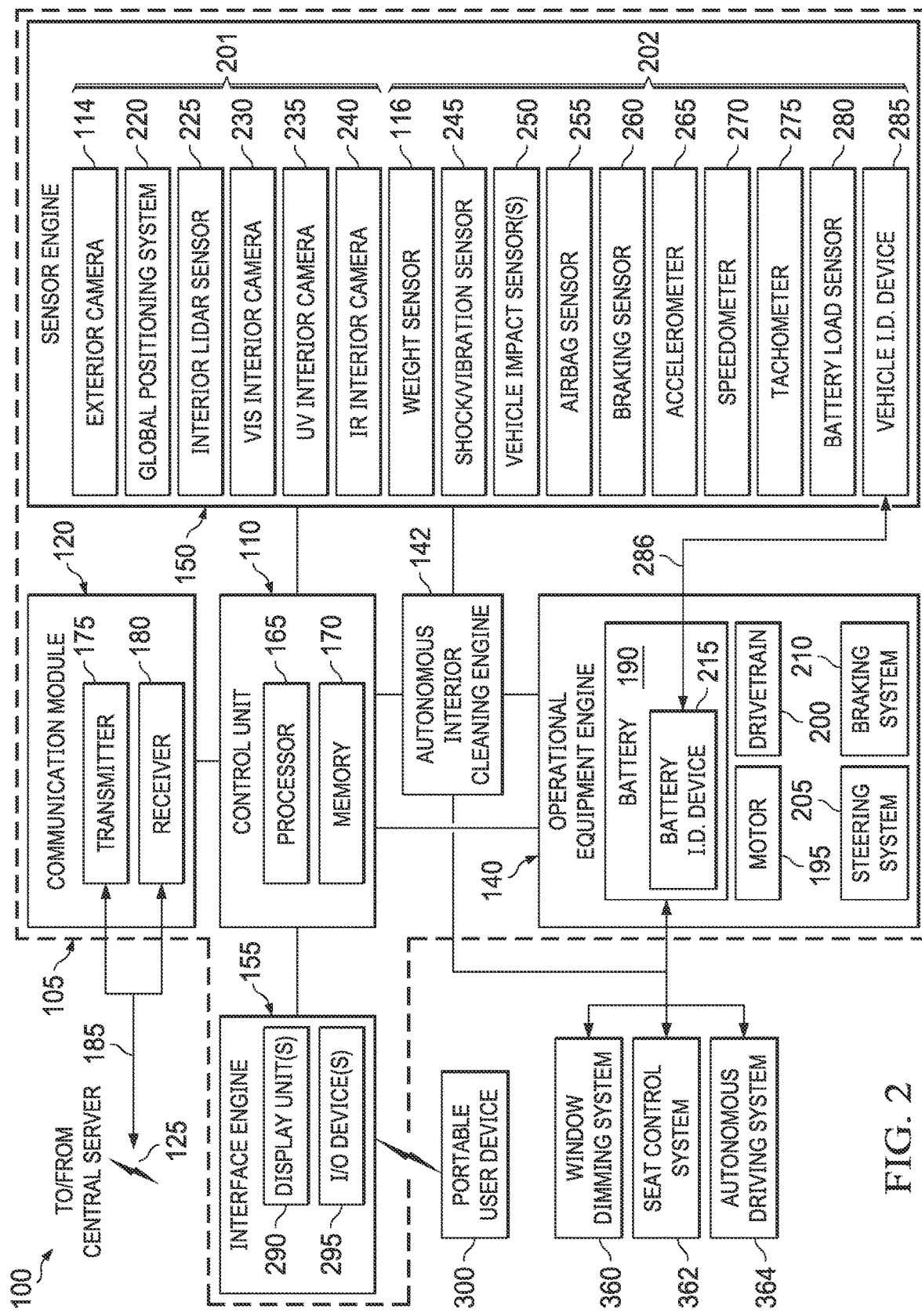
FIG. 2 is a diagrammatic illustration, in a block-diagram form, of at least a portion of the autonomous vehicle cleaning system of FIG. 1, in accordance with at least one embodiment of the present disclosure.

FIG. 2 is a diagrammatic illustration, in a block-diagram form, of at least a portion of the autonomous vehicle cleaning system 100 of FIG. 1, in accordance with at least one embodiment of the present disclosure. It is noted that the components of the vehicle 105 may be located either permanently or temporarily as a part of the vehicle 105. The vehicle control unit (VCU) 110 includes a processor 165 and a memory 170. In some examples, the communication module 120, which is operably coupled to, and adapted to be in communication with, the vehicle control unit 110, includes a transmitter 175 and a receiver 180. In some examples, one or the other of the transmitter 175 and the receiver 180 may be omitted according to the particular application for which the communication module 120 is to be used. In other examples, the transmitter 175 and receiver 180 are combined into a single transceiver that performs both transmitting and receiving functions.

In some examples, the operational equipment engine 140, which is operably coupled to, and adapted to be in communication with, the vehicle control unit 110, includes a plurality of devices configured to facilitate driving of the vehicle 105. In this regard, the operational equipment engine 140 may be designed to exchange communication with the vehicle control unit 110, so as to not only receive instructions, but to provide information on the operation of the operational equipment engine 140. For example, the operational equipment engine 140 may include a vehicle battery 190, a motor 195, a drivetrain 200, a steering system 205, and a braking system 210. In some vehicles, the vehicle battery 190 may provide electrical power to the motor 195 to drive the wheels 115e of the vehicle 105 via the drivetrain 200. In some examples, instead of or in addition to providing power to the motor 195 to drive the wheels 115e of the vehicle 105 via the drivetrain or transmission 200, the vehicle battery 190 provides electrical power to another component of the operational equipment engine 140, the vehicle control unit 110, the communication module 120, the sensor engine 150, the interface engine 155, or any combination thereof. In some examples, the vehicle battery 190 includes a battery identification device 215. In some embodiments, the motor is an internal combustion motor and the battery operates a starter.

In some examples, the sensor engine 150, which is operably coupled to, and adapted to be in communication with, the vehicle control unit 110, includes devices such as sensors, meters, detectors, or other devices configured to measure or sense a parameter related to a driving operation or other operation of the vehicle 105. For example, the sensor engine 150 may include a global positioning system 220, an interior lidar sensor 225, a visible light interior camera 230, an ultraviolet (UV) interior camera 235, an infrared interior camera 240, a shock/vibration sensor 245, a vehicle impact sensor 250, an airbag sensor 255, a braking sensor 260, an accelerometer 265, a speedometer 270, a tachometer 275, a battery load sensor 280, a vehicle identification device 285, an exterior camera 114, a weight sensor 116, or any combinations thereof. Any of the visible light interior camera 230, an ultraviolet (UV) interior camera 235, an infrared interior camera 240 may be employed as a light sensor for determining the amount of light that is present in the vehicle interior, or a separate light sensor may be provided. The sensors or other detection devices may be configured to sense or detect activity, conditions, and circumstances in an area to which the device has access, e.g., conditions inside or outside the vehicle cabin. Such sensors may include, but are not limited to, angle sensors, rotary encoders, or linear encoders. Sub-components of the sensor engine 150 may be deployed at any operational area where information on the status of the vehicle 105 may occur. Readings from the sensor engine 150 may be fed back to the vehicle control unit 110, or other control units. Stored and reported performance data may include the sensed data, or may be derived, calculated, or inferred from sensed data. The vehicle control unit 110 may send signals to the sensor engine 150 to adjust calibration or operating parameters of the sensor engine 150 in accordance with a control program in the vehicle control unit 110. The vehicle control unit 110 is adapted to receive and process performance data from the sensor engine 150 or from other suitable source(s), and to monitor, store (e.g., in the memory 170), and/or otherwise process (e.g., using the processor 165) the received performance data.

The braking sensor 260 is adapted to monitor usage of the vehicle 105's braking system 210 (e.g., an antilock braking system 210) and to communicate the braking information to the vehicle control unit 110. The accelerometer 265 is adapted to monitor acceleration of the vehicle 105 and to communicate the acceleration information to the vehicle control unit 110. The accelerometer 265 may be, for example, a two-axis accelerometer 265 or a three-axis accelerometer 265. In some examples, the accelerometer 265 is associated with an airbag of the vehicle 105 to trigger deployment of the airbag. The speedometer 270 is adapted to monitor speed of the vehicle 105 and to communicate the speed information to the vehicle control unit 110. In some examples, the speedometer 270 is associated with a display unit of the vehicle 105 such as, for example, a display unit of the interface engine 155, to provide a visual indication of vehicle speed to a driver of the vehicle 105. The tachometer 275 is adapted to monitor the working speed (e.g., in revolutions-per-minute) of the vehicle 105's motor 195 and to communicate the angular velocity information to the vehicle control unit 110. In some examples, the tachometer 275 is associated with a display unit of the vehicle 105 such as, for example, a display unit of the interface engine 155, to provide a visual indication of the motor 195's working speed to the driver of the vehicle 105. The battery load sensor 280 is adapted to monitor charging, discharging, and/or overcharging of the vehicle battery 190 and to communicate the charging, discharging, and/or overcharging information to the vehicle control unit 110.

In some examples, the vehicle identification device 285 stores data identifying the vehicle 105 such as, for example, manufacturing information (e.g., make, model, production date, production facility, etc.), vehicle characteristic(s) information, vehicle identification number ("VIN") information, battery compatibility information, or the like. The vehicle identification device 285 is adapted to communicate with the battery identification device 215 (or vice versa), as indicated by arrow 286. In some examples, the vehicle identification device 285 and the battery identification device 215 may each communicate with the vehicle control unit 110.

In some examples, the interface engine 155, which is operably coupled to, and adapted to be in communication with, the vehicle control unit 110, includes at least one input and output device or system that enables a user to interact with the vehicle control unit 110 and the functions that the vehicle control unit 110 provides. For example, the interface engine 155 may include a display unit 290 and an input/ output ("I/O") device 295. The display unit 290 may be, include, or be part of multiple display units. In some examples, the display unit 290 may include one, or any combination, of a central display unit associated with a dash of the vehicle 105, an instrument cluster display unit associated with an instrument cluster of the vehicle 105, and/or a heads-up display unit associated with the dash and a windshield of the vehicle 105; accordingly, as used herein the reference numeral 290 may refer to one, or any combination, of the display units. The I/O device 295 may be, include, or be part of a communication port (e.g., a USB port), a Bluetooth communication interface, a touch-screen display unit, soft keys associated with a dash, a steering wheel, or another component of the vehicle 105, and/or similar components. Other examples of sub-components that may be part of the interlace engine 155 include, but are not limited to, audible alarms, visual alerts, telecommunications equipment, and computer-related components, peripherals, and systems.

In some examples, a portable user device 300 belonging to an occupant of the vehicle 105 may be coupled to, and adapted to be in communication with, the interface engine 155. For example, the portable user device 300 may be coupled to, and adapted to be in communication with, the interface engine 155 via the I/O device 295 (e.g., the USB port and/or the Bluetooth communication interface). In an example, the portable user device 300 is a handheld or otherwise portable device (e.g., a smartphone or tablet computer) which is carried onto the vehicle 105 by a user who is a driver or a passenger on the vehicle 105, or proximate to the vehicle. In addition, or instead, the portable user device 300 may be removably connectable to the vehicle 105, such as by temporarily attaching the portable user device 300 to the dash, a center console, a seat back, or another surface in the vehicle 105. In another example, the portable user device 300 may be permanently installed in the vehicle 105. In some examples, the portable user device 300 is, includes, or is part of one or more computing devices such as personal computers, personal digital assistants, cellular devices, mobile telephones, wireless devices, handheld devices, laptops, audio devices, tablet computers, game consoles, cameras, and/or any other suitable devices. In several examples, the portable user device 300 is a smartphone such as, for example, an iPhone® by Apple Incorporated.

The autonomous vehicle cleaning system 100 also includes an autonomous interior cleaning engine 142, seat control system 360, window dimming system 362, and autonomous driving system 364, the operation of which will be described below. In some embodiments, the autonomous interior cleaning engine 142 comprises a standalone housing which may in some cases include a processor and memory. In other embodiments, the autonomous interior cleaning engine 142 may be operated by software, firmware, or hardware within another processor, such as the vehicle control unit 110, operational equipment engine 140, or power train ECU 113. The sensor engine 150 includes environmental sensors 201 and vehicle sensors 202. In an example, the autonomous interior cleaning engine 142 receives sensor data from one or more sensors.

A reader of ordinary skill in the art will understand that other components or arrangements of components may be found in a vehicle 105, and that the same general principles apply to electric vehicles, internal combustion vehicles, and hybrid vehicles.

Figure 3:
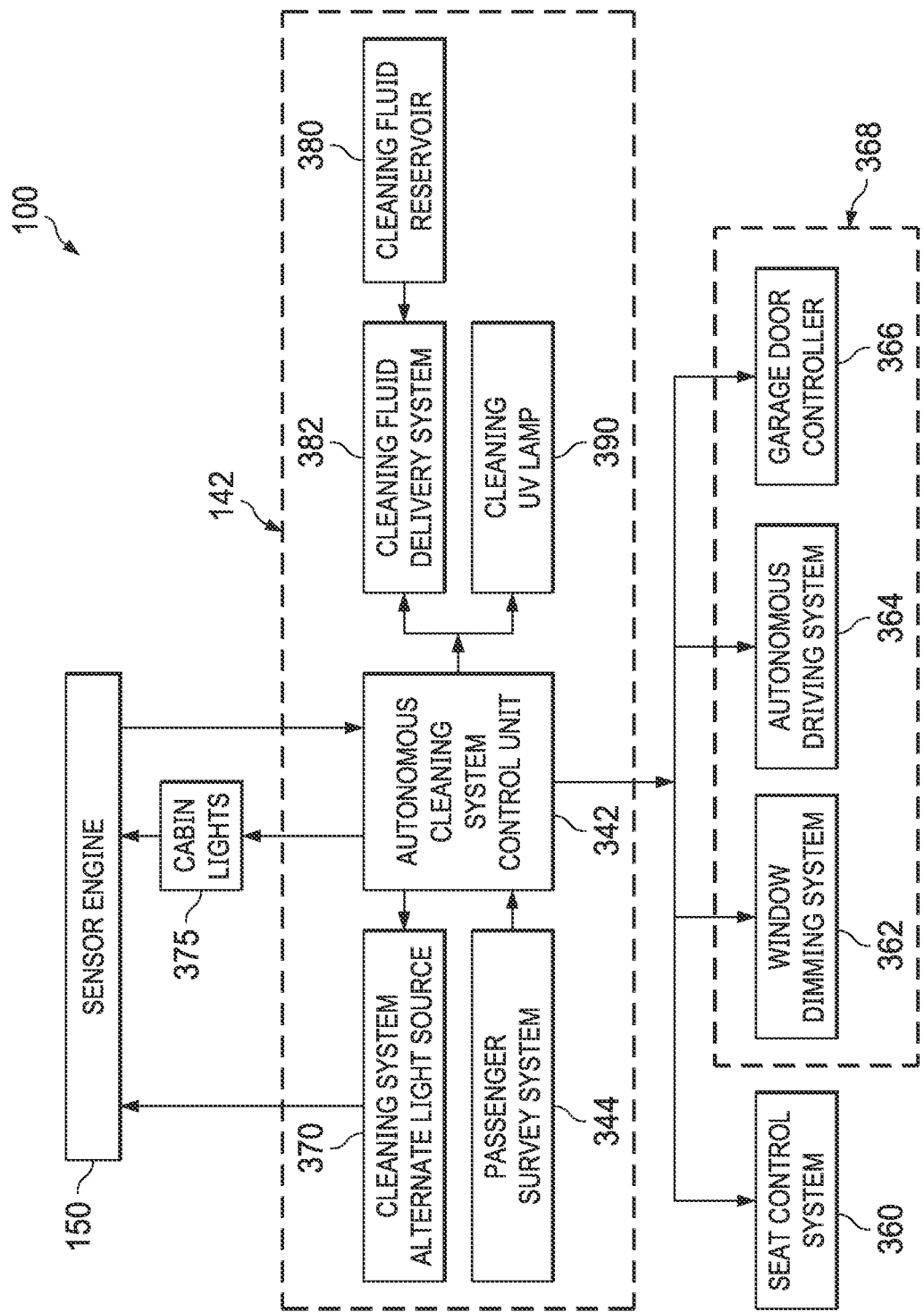
FIG. 3 is a schematic view, in block diagram form, of at least a portion of an example autonomous vehicle cleaning system with adjustable ground truth, in accordance with at least one embodiment of the present disclosure.

FIG. 3 is a schematic view, in block diagram form, of at least a portion of an example autonomous vehicle cleaning system 100 with adjustable ground truth, in accordance with at least one embodiment of the present disclosure. In the example shown in FIG. 3, the autonomous vehicle cleaning system 100 includes an autonomous interior cleaning engine 142, which receives sensor information from the sensor engine 150. Such sensor information may include for example images from an interior lidar sensor 225, an interior visible light camera 230, an interior ultraviolet (UV) camera 235, or an interior near-infrared (NIR) camera 240. In some embodiments, two or more of the visible light camera 230, ultraviolet camera 235, or infrared camera 240 may be the same camera, operating with interchangeable filters or sensor elements.

The autonomous interior cleaning engine 142 includes a passenger survey system 344 that is capable of receiving passenger input regarding the cleanliness of the vehicle. The passenger input is then used to gauge whether the vehicle needs to be cleaned. The autonomous interior cleaning engine 142 may also include various elements for inspecting and cleaning the interior of the vehicle. In the example shown in FIG. 3, the autonomous interior cleaning engine 142 includes an autonomous cleaning system control unit 342 (e.g., a processor with a memory), along with a cleaning system alternate light source 370, a cleaning fluid reservoir 380 and cleaning fluid delivery system 382, and a cleaning UV lamp 390, any of which may be activated by the autonomous cleaning system control unit 342 at different times, as described below. The autonomous cleaning system control unit 342 may also activate: a seat control system 360 to control the position and recline of vehicle seats; a window dimming system 362 to darken the vehicle windows and thus darken the interior of the vehicle; and an autonomous driving system 364 to instruct the vehicle to darken the interior of the vehicle by driving to a darkened area such as a tunnel or parking garage. Alternatively, the autonomous cleaning system control unit 342 may instruct a human driver (e.g., via the interface engine 155, portable user device 300, or communication module 120) to drive to a desired location, possibly with the aid of a global positioning system 220. In some embodiments, the window dimming system controls the dimming of the windows through automatic shades, louvres, curtains, visors, or electrochromic elements coated onto or embedded within the windows, or other devices that have the effect of altering the amount of light from external sources (e.g., sunlight) that is able to enter the vehicle interior.

The autonomous cleaning system control unit 342 may detect trash or other foreign objects using the lidar sensor 225, by capturing a current 3D image or point cloud of the vehicle interior and comparing it to a stored baseline or nominal point cloud of an empty vehicle. The autonomous cleaning system control unit 342 may also detect stains and spills using an image from the visible light interior camera 230, ultraviolet interior camera 235, or infrared interior camera 240. If differences between the captured images and the stored baseline images exceed an adjustable threshold, then the differences are assumed to be foreign material. One way to calculate the adjustable threshold is to do image subtraction of the capture image from the stored baseline. Image segmentation can then be applied to the resulting subtracted image to determine if any large, continuous differences exist. An object or dirt area will result in a large continuous difference in the segmented image. In some cases, a small misalignment may happen between the images, causing small regions of difference in the segmented image. The threshold can then be set based on the area sizes in the segmented image, such that it is triggered only by large, continuous areas, and ignores small differences attributable to misalignment. In some embodiments, algorithms such as expert systems, machine learning, or other artificial intelligence may be used to determine if segmented areas are attributable to noise or to a dirty area within the vehicle interior.

A visible light camera 230 may image the vehicle interior using visible light emitted by the cabin lights 375, which may be switched on or off by the autonomous cleaning system control unit 342. In some embodiments, the visible light camera may include one or more swappable or non-swappable filters to restrict certain wavelengths of light. An ultraviolet interior camera 235 or infrared interior camera 240 may image the interior using ultraviolet light or infrared light emitted by the cleaning system alternate light source 370, which may for example be a blue lamp emitting at a wavelength of 450-490 nanometers (nm), a violet lamp emitting at a wavelength of 400-450 nm, a near-UV (NUV) lamp emitting at a wavelength of 260-400 nm, or a near-infrared (NIR) lamp emitting at a wavelength of 800-1600 nm. In an example a NIR lamp may emit at, and a NIR camera may image at, a wavelength of 800 nm, 1310 or 1550 nm, which have shown utility for imaging stains and for showing contrast between differing materials that may, to the human eye under visible light, appear to be the same color.

An alternate light source 370 comprising a blue, violet, or UV lamp may cause certain stains or spills to fluoresce, such that they can be imaged by a visible light camera 230, with or without a filter, even if the stains would be difficult to resolve with a visible light camera under ambient (e.g., white) light. If the passenger survey data indicates that the vehicle needs cleaning, but the sensor data fails to corroborate this, the autonomous vehicle cleaning system 100 may elect either to clean the vehicle or not to clean the vehicle (e.g., based on a system setting). If passenger survey data consistently indicates that the vehicle does not require cleaning, but the sensor data indicates the presence of detectable discolorations or shape anomalies in the vehicle interior, then the autonomous vehicle cleaning system 100 may classify the discolorations or shape anomalies as wear defects (e.g., as not being cleanable foreign material), and may save new ground truth images incorporating these features, such that they are ignored by future sensor scans of the vehicle interior.

A UV cleaning lamp 390 may for example emit UV-A radiation at a wavelength of 315-400 nm, UV-B radiation at a wavelength of 280-315 nm, or UV-C radiation at a wavelength of 100-280 nm. UV-C radiation may be more effective than UV-A or UV-B at killing or inactivating microorganisms, breaking down organic molecules, and bleaching out stains, but may also accelerate aging of materials (e.g., polymers) comprising the automotive interior. Ultraviolet light may be harmful to humans, and may therefore be activated by the autonomous cleaning system control unit 342 only when the control unit 342 has confirmed that no humans are present within the vehicle, and that all doors and windows are closed. In some embodiments, an alternate light source UV lamp 370 and a cleaning UV lamp 390 may be the same lamp. Not all of the elements shown will necessarily be present in a given embodiment. Other elements or components may be present instead of or in addition to those shown, and the arrangement or relationships between the elements may differ, without departing from the spirit of the present disclosure. Some elements may be combined. For example, in some embodiments, the autonomous cleaning system control unit 342 may be incorporated into the vehicle control unit 110.

In some instances, a window dimming system 362 and autonomous driving system 364 may both be components of an external light control system 368, whose purpose is to control the amount of external light (e.g., sunlight) entering the vehicle interior. In some embodiments, the external light control system may include other features, such as an automatic garage door controller 366 capable of opening or closing a garage door, or commanding a garage door to open or close, in order to adjust the amount of external light entering the vehicle interior.

Figure 4:
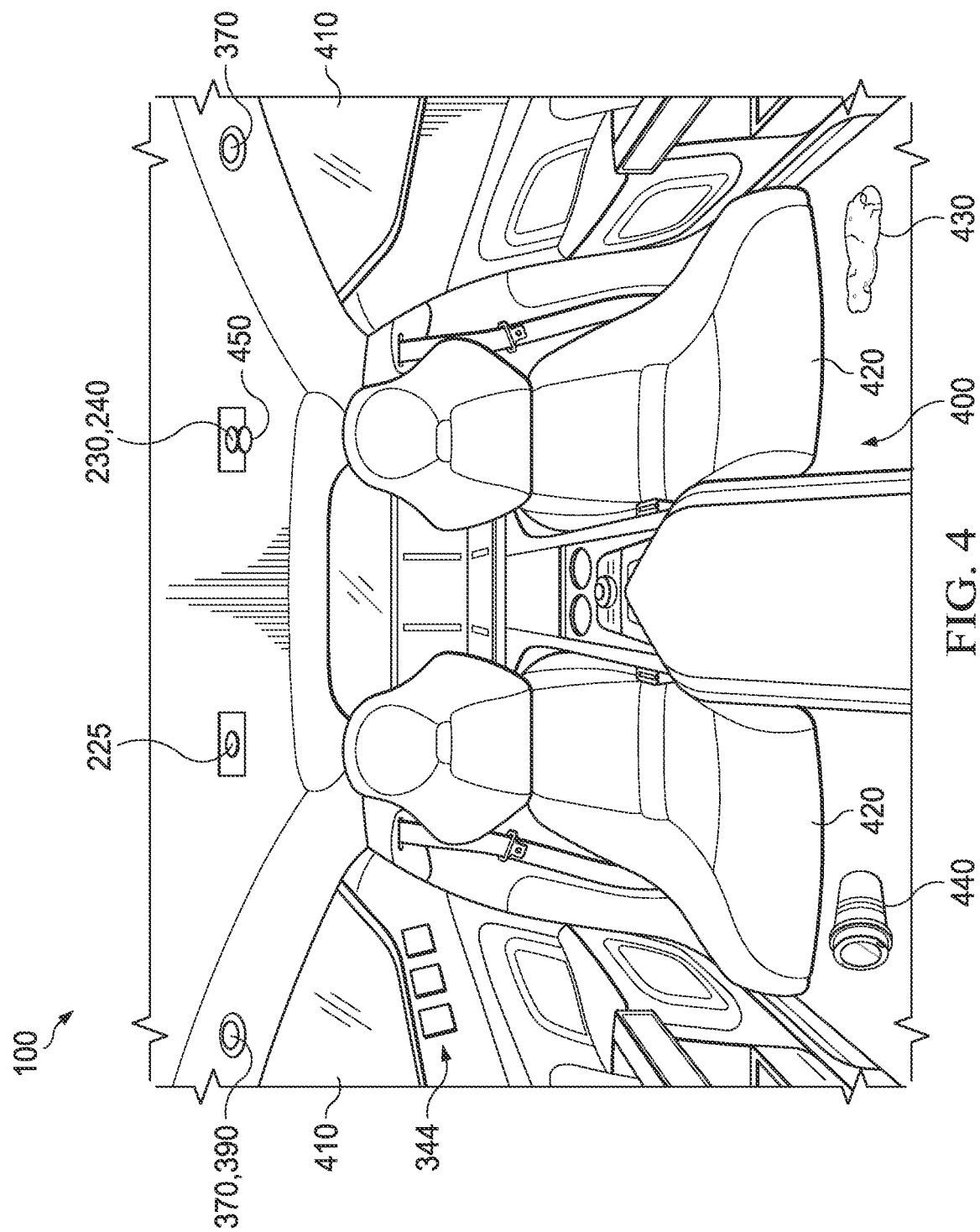
FIG. 4 is a perspective view of a vehicle interior incorporating at least a portion of an example autonomous vehicle cleaning system with adjustable ground truth, in accordance with at least one embodiment of the present disclosure.

FIG. 4 is a perspective view of a vehicle interior 400 incorporating at least a portion of an example autonomous vehicle cleaning system 100 with adjustable ground truth, in accordance with at least one embodiment of the present disclosure. In the example shown in FIG. 4, the autonomous vehicle cleaning system 100 includes a passenger survey system 344, as well as dimmable windows 410, a combined UV alternate light source 370 and UV cleaning lamp 390, an interior lidar 225, a combined visible light interior camera 230 and infrared interior camera 240 with an automatically swappable filter 450, and an infrared alternate light source 370.

The vehicle interior 400 also includes movable seats 420, which can be controlled via the seat control system 360 under the command of the autonomous cleaning system control unit 342. For example, the seats 420 may be moved forward, moved backward, folded, unfolded, reclined, un-reclined, raised, or lowered in order to access to different parts of the vehicle interior 400. For example, moving the seats may permit the lidar 225 and the camera 230, 240 to image different portions of the vehicle interior 400, and also permit the cleaning UV lamp 390, or a cleaning fluid delivery system 382, to clean different portions of the vehicle interior 400. In an example, a surface of the vehicle interior 400 includes a stain 430 which is visible to the camera 230, 240 only when the seats 420 are moved all the way backward. Other possible stains 430 might be visible to the camera 230, 240 when the seats are forward, folded, unfolded, raised, reclined, or otherwise. In this example, a surface of the vehicle interior 400 also includes a foreign object 440 (e.g., a cup, wrapper, receipt, etc.) that is visible to the camera 230, 240, and/or the lidar 225, only when the seats 420 are in certain positions.

Figure 5:
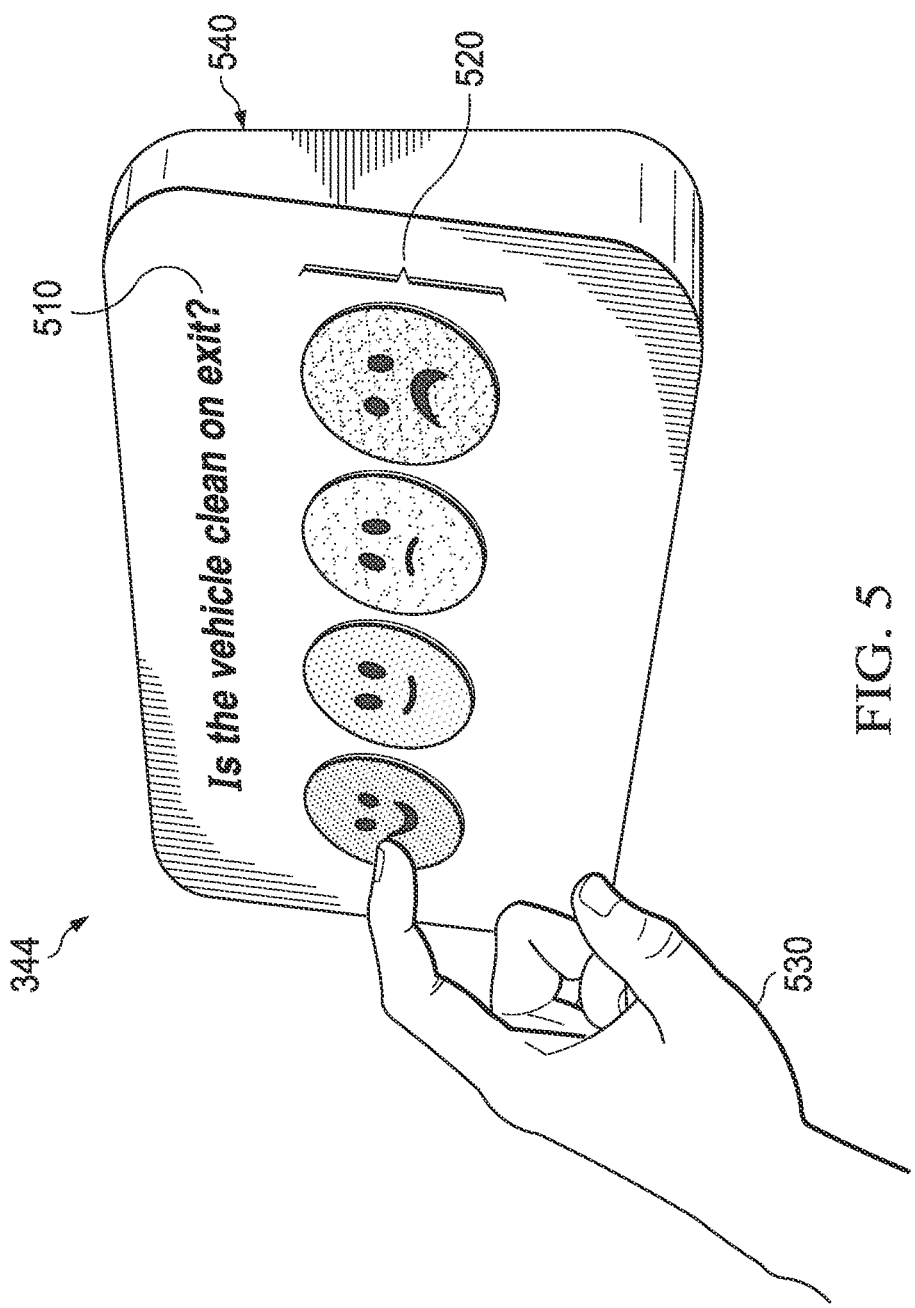
FIG. 5 is a perspective view of an example passenger survey system of an autonomous vehicle cleaning system with adjustable ground truth, in accordance with at least one embodiment of the present disclosure.

FIG. 5 is a perspective view of an example passenger survey system 344 of an autonomous vehicle cleaning system 100, in accordance with at least one embodiment of the present disclosure. In some embodiments, the passenger survey system 344 includes text 510 and buttons 520. The text 510 may for example include instructions to a user 530 to select a perceived cleanliness level of the vehicle. The text 510 may be fixed, manually changeable, or automatically changeable, and may be illuminated or non-illuminated. When the user 530 presses a button 520, the resulting user feedback is sent to the autonomous cleaning system control unit 342, which generates an appropriate action. In some embodiments, the autonomous cleaning system control unit 342 may respond immediately to reports of a dirty vehicle, by initiating a procedure as shown for example in FIG. 6, below. In other embodiments, actions by the autonomous cleaning system control unit 342 and autonomous vehicle cleaning system 100 are based only on the input of two or more users. This may for example help reduce unnecessary cleaning of the vehicle by reducing the impact of subjectivity on the part of users 530, and/or reduce the effect of accidental, erroneous, or unserious button presses.

The passenger survey system 344 may for example exist as a touchscreen user interface with soft buttons 520 (e.g., running on a display unit 290 under control of the interface engine 155, or on a portable user device 300), or may exist as a standalone module that includes a housing 540 and electromechanical buttons 520. In other embodiments, the passenger survey system 344 may include a voice interface, gesture interface, or any other interface capable of serving the defined function of soliciting passenger feedback as to the cleanliness of the vehicle. In some embodiments, the survey may be sent to a passenger's mobile device.

Figure 6:
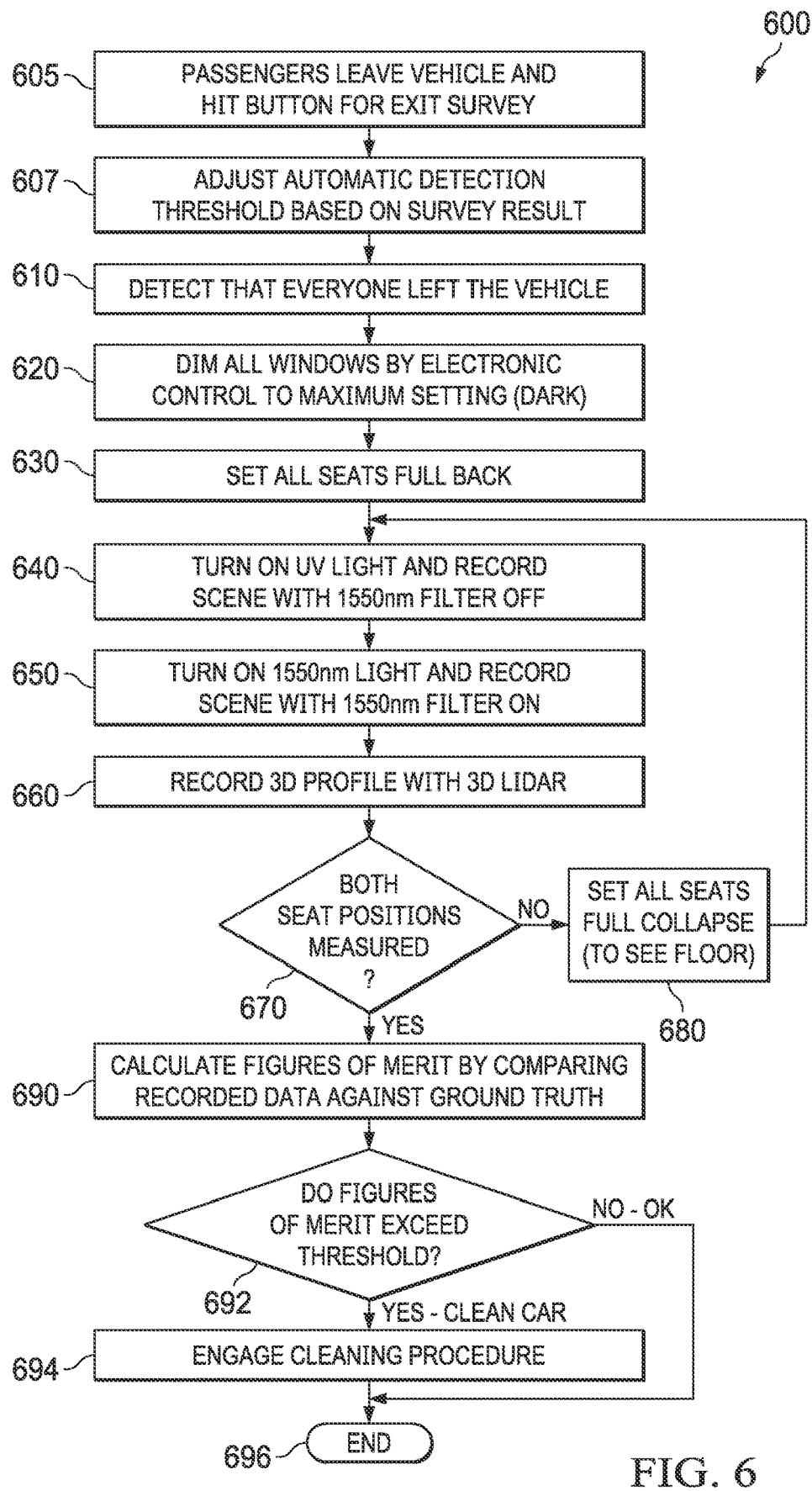
FIG. 6 is a flow diagram showing an example autonomous vehicle cleaning method with adjustable ground truth, in accordance with at least one embodiment of the present disclosure.

FIG. 6 is a flow diagram showing an example autonomous vehicle cleaning method 600 with adjustable ground truth, in accordance with at least one embodiment of the present disclosure. It should be understood that the steps of method 600 may be performed in a different order than shown in FIG. 6, additional steps can be provided before, during, and after the steps, and/or some of the steps described can be replaced or eliminated in other embodiments. One or more of steps of the method 600 can be carried by one or more devices and/or systems described herein, such as elements of the sensor engine 150, vehicle control unit 110, autonomous interior cleaning engine 142, autonomous cleaning system control unit 342, seat control system 360, window dimming system 362, autonomous driving system 364, or other elements or processors present in the vehicle, as appropriate.

In step 605, the method 600 includes receiving user input about the cleanliness of the vehicle interior, for example in the form of an exit survey via the passenger survey system (as shown for example in FIG. 5). In some embodiments, passengers may have the option to point out specific areas on the vehicle that need to be cleaned. Execution then proceeds to step 607.

In step 607, the method 600 adjusts one or more automatic detection thresholds based on the user input. For example, if the user input indicates that the vehicle interior is dirty, the detection thresholds may be reduced such that foreign material is more easily detected. If the user input indicates that the vehicle interior is clean, the detection thresholds may be increased such that foreign material is less easily detected. In some embodiments, users may be provided with multiple choices, each of which has a different effect on the detection thresholds. In some embodiments, if multiple users report the vehicle interior as clean, new baseline images may be captured and stored to reflect the current condition of the vehicle as it accumulates wear defects due to normal wear and tear. Conversely, if multiple users report the vehicle as dirty, even after multiple cleaning attempts, the method may schedule a visit with a service location for manual evaluation and/or manual cleaning of the vehicle interior. In such a case, the method may also command navigation to the service location via the autonomous driving system.

Once step 607 is complete, execution proceeds to step 610.

In step 610, the method 600 includes detecting whether the vehicle is empty of human or animal occupants. Such detection may involve interior lidar sensor 225 or cameras 230, 235, or 240, along with an image recognition, shape recognition, or movement recognition algorithm running on the VCU 110, autonomous cleaning system control unit 342, or other processor. If human or animal occupants are detected within the vehicle, step 610 may continue or repeat until the vehicle is detected to be empty, at which point execution proceeds to step 620.

In step 620, the amount of light entering the vehicle interior is optimized. Optimization or control of the amount of external light entering the vehicle interior may for example be effected by an external light control system 368 or autonomous cleaning system control unit 342, as shown for example in FIG. 3, or vehicle control unit 110 as shown for example in FIG. 2. In some embodiments, optimization may be accomplished for example by measuring the amount of light inside or outside the vehicle using an exterior camera 114 or interior visible light camera 230, and then setting the dimmable windows 410 (whether electrochromically or by other means) to a desired amount of light transmission. In other embodiments this light optimization may be accomplished by instructing an autonomous driving system 364 (as shown for example in FIG. 3) to drive the vehicle to an area (e.g., a tunnel or parking garage) that has a desired amount of external light. In still other embodiments, dimming may be accomplished by waiting until a particular time of day, or by opening or closing a garage door. Once the vehicle interior is suitably illuminated, execution proceeds to step 630.

In step 630, vehicle seats 420 are moved to desired positions (e.g., all the way forward or all the way back) to expose, for inspection and cleaning, certain surfaces or portions of surface of the vehicle interior 400. This may be accomplished for example through commands sent from the autonomous cleaning system control unit 342 to the seat control system 360. Execution then proceeds to step 640.

In step 640, the scene is imaged with a camera and light source, in order to look for stains, spills, dirt, mud, or other foreign material. This may for example involve activating a blue, violet, or UV alternate light source 370 and imaging the vehicle interior 400 with a visible light camera 230, with or without a filter (e.g., an orange or yellow bandpass filter to exclude the blue, violet, or UV light of the alternate light source). Such an arrangement may cause certain materials to fluoresce such that they emit visible light and are more easily distinguished from the vehicle materials on which they have been deposited. In this sense, the visible light emitted by foreign materials may be considered to have been generated by the alternate light source. Current images captured by the camera can then be compared against a stored baseline image of a clean vehicle (e.g., captured with the same camera and light source), such that differences between the current image and the baseline image, that exceed a given threshold, can be identified as stains or spills. Execution then proceeds to step 650.

In step 650, the scene is imaged with a combination of camera and light source (e.g., different than the combination of camera and light source employed in step 640), in order to look for stains, spills, dirt, mud, or other foreign material. This may for example involve activating an infrared light source 370 and imaging the vehicle interior 400 with an infrared camera 240, with or without a filter (e.g., an infrared bandpass filter to exclude all wavelengths except that of the IR lamp 370). Such an arrangement may cause certain dirt, stain, or spill materials to stand out (e.g., as light or dark spots) against the materials of the vehicle interior, even if, under white light with a visible light camera, they would appear to be the same color. Current images captured in this way can then be compared against a stored baseline image of a clean vehicle (e.g., captured with the same camera and light source), such that differences between the current image and the baseline image, which exceed a specified threshold that may be the same as or different than the threshold of step 640, can be identified as stains or spills. Execution then proceeds to step 660.

In step 660, the vehicle interior is imaged (e.g., as a point cloud) using a 3D sensing device such as a lidar 225, although other sensing devices may be used instead or in addition, including a 3D camera, radar, or sonar. In some embodiments, the 3D sensor may be the same as the camera employed in steps 640 or 650. The resulting current 3D image can then be compared against a stored baseline 3D image, and any differences between the current image and the baseline image, which exceed a given threshold that may be the same as or different than the threshold of steps 640 and 650, can be identified as trash, debris, or other foreign material. Execution then proceeds to step 670.

In step 670, the method determines whether the vehicle interior has been imaged in all desired seat positions. If the answer is no, execution proceeds to step 680. If the answer is yes, execution proceeds to step 690.

In step 680, the vehicle seats 420 are moved to a new desired position (e.g., all the way forward, all the way folded, etc.), and execution then returns to step 640.

In step 690, the vehicle interior has been imaged in all desired seat positions, and the locations of dirt, dust, stains, spills, trash, debris, and other foreign material have been identified. The method then calculates one or more Figures of Merit (FOMs), by comparing the images captured in steps 640, 650, and 660 against their stored baselines. One way to determine the FOM is to create a linear combination of all subtracted segmented areas. Each segmented area can then be weighted. In some embodiments, the weights may represent the size of the area, or the probability the area is a dirt spot based on an algorithm as described above. When more segmented regions are detected, or when their computed size or severity is larger, the FOM increases to indicate a dirtier vehicle. Execution then proceeds to step 692.

In step 692, the method determined whether one or more FOMs exceed their respective automatic detection thresholds. If no, then execution proceeds to step 696. If yes, execution proceeds to step 694.

In step 694, the method engages a cleaning procedure. In some embodiments, the cleaning procedure may involve activation for a set period of time of a cleaning element. The cleaning element may for example be a UV cleaning lamp 390 or a cleaning fluid delivery system 382 such as a spray nozzle that draws fluid (e.g., solvents, antiseptics, degreasers, deodorizers, or perfumes) from a cleaning fluid reservoir 380. The cleaning element is then turned off either after a predetermined time or a calculated time for cleaning based on how dirty the car is. In some embodiments, seats may be moved to various positions again during the cleaning procedure, in order to clean all areas accessible to the cleaning element. In other embodiments, the cleaning procedure may involve notifying a service crew (e.g., via the communications module 120) of the presence and locations of foreign material and then instructing the autonomous driving system 364 to drive the vehicle to the service location. In still other embodiments, the cleaning procedure may involve notifying a vehicle owner or operator (e.g., via the communications module 120, or via a display under the control of the interface engine 155 or portable user device 300) of the presence and locations of foreign material, and permitting the vehicle owner or operator to take appropriate action.

Once step 694 is complete, execution proceeds to step 696.

In step 696, the method is complete, but may be re-activated (or execution transferred back to step 605) when certain conditions are met, such as when new passengers are delivered to their destination.

In some embodiments, method 600 is activated once, after the vehicle has arrived at a destination. In other embodiments, the method 600 may be activated multiple times, to assess the success of previous cleaning attempts. In some embodiments, depending on the locations of foreign material in the vehicle interior, the cleaning procedure may be activated multiple times while the seats are in different positions.

Figure 7:
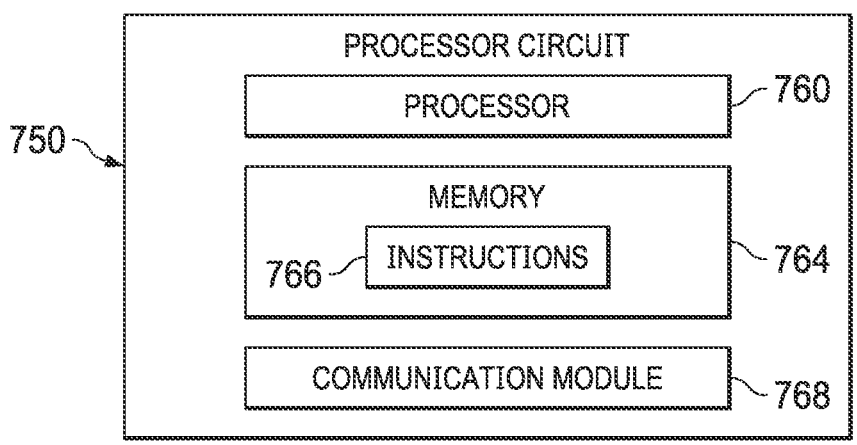
FIG. 7 is a diagrammatic illustration of a processor circuit, according to embodiments of the present disclosure.

FIG. 7 is a diagrammatic illustration of a processor circuit 750, according to embodiments of the present disclosure. The processor circuit 750 may be implemented in the autonomous vehicle cleaning system 100, VCU 110, portable device 300, or other devices or workstations (e.g., third-party workstations, network routers, etc.), or on a cloud processor or other remote processing unit, as necessary to implement the method. As shown, the processor circuit 750 may include a processor 760, a memory 764, and a communication module 768. These elements may be in direct or indirect communication with each other, for example via one or more buses.

The processor 760 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 760 may also comprise another hardware device, a firmware device, or any combination thereof configured to perform the operations described herein. The processor 760 may also be implemented as a combination of computing devices, e.g., a combination of a DSP and a microprocessor, a plurality of microprocessors, one or more microprocessors in conjunction with a DSP core, or any other such configuration.

The memory 764 may include a cache memory (e.g., a cache memory of the processor 860), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 764 includes a non-transitory computer-readable medium. The memory 764 may store instructions 766. The instructions 766 may include instructions that, when executed by the processor 760, cause the processor 760 to perform the operations described herein. Instructions 766 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 768 can include any electronic circuitry and/or logic circuitry to facilitate direct or indirect communication of data between the processor circuit 750, and other processors or devices. In that regard, the communication module 768 can be an input/output (I/O) device. In some instances, the communication module 768 facilitates direct or indirect communication between various elements of the processor circuit 750 and/or the autonomous vehicle interior cleaning engine 142. The communication module 768 may communicate within the processor circuit 750 through numerous methods or protocols. Serial communication protocols may include but are not limited to US SPI, I$^2$C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and a central server, or readings from the sensors) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

As will be readily appreciated by those having ordinary skill in the art after becoming familiar with the teachings herein, the autonomous vehicle cleaning system advantageously permits a MaaS vehicle to clean itself in between passenger pickups, even in hard-to-reach areas, and/or to identify messes that require human intervention to clean, and to deliver the vehicle to a service location with detailed instructions as to the locations of the foreign material. A number of variations are possible on the examples and embodiments described above. For example, other elements, or other combinations of elements, may be present in the automotive interior 400 or autonomous interior cleaning engine 142 to achieve the desired result of autonomous cleaning of the vehicle interior. Such elements may include for example other sensors, other light sources, other cleaning agents, and other means of controlling interior lighting. Elements can vary in size, shape, position, mechanism of operation, and mode of operation without departing from the spirit of the present disclosure. Multiple cleaning mechanisms can be provided. The technology described herein may be applied to myriad different vehicle types, including internal combustion, electric, and hybrid vehicles, cars, trucks, vans, campers, and other vehicles, including off-road vehicles, aircraft, watercraft, or spacecraft, whether manually operated, driver-tended, fully autonomous, or MaaS.

The logical operations making up the embodiments of the technology described herein are referred to variously as operations, steps, objects, elements, components, or modules. It should be understood that these may be performed in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the autonomous vehicle cleaning system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." The word "comprising" does not exclude other elements or steps, and the indefinite article "a" or "an" does not exclude a plurality. Unless otherwise noted in the claims, stated values shall be interpreted as illustrative only and shall not be taken to be limiting.

The above specification, examples and data provide a complete description of the structure and use of exemplary embodiments of the autonomous vehicle cleaning system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. A vehicle comprising:
   an interior and an exterior;
   a surface disposed within the interior;
   a processor;
   a non-lidar light source configured to illuminate the surface, wherein the non-lidar light source comprises a blue light source, a violet light source, a near-infrared light source, or a near-ultraviolet light source;
   a sensor configured to, under control of the processor, capture an image of the surface while the surface is illuminated by the non-lidar light source; and
   a stored image of the surface;
   a detection threshold; and
   a passenger survey system configured to receive an input from a passenger regarding cleanliness of the surface,
      wherein the processor is configured to adjust the detection threshold based on the input;
      wherein the processor is configured to detect foreign material on the surface based on the detection threshold and a comparison between the captured image and the stored image,
      wherein the processor is configured to, after detecting the foreign material on the surface, indicate that the vehicle needs to be cleaned.

2. The vehicle of claim 1, wherein the passenger survey system is disposed within the interior of the vehicle, and wherein the vehicle further comprises a cleaning element configured to, when activated by the processor indicating that the vehicle needs to be cleaned, clean the surface.

3. The vehicle of claim 2, wherein the passenger survey system comprises a touchscreen, a voice interface, a gesture interface, or a housing comprising electromechanical buttons.

4. The vehicle of claim 2, wherein the processor is configured to activate the cleaning element for:
   a fixed period of time,
   a period of time based on the input, or
   a period of time based on a property of the detected foreign material.

5. The vehicle of claim 2, wherein the cleaning element is a UV lamp or a cleaning fluid delivery system.

6. The vehicle of claim 1, further comprising:
   a movable seat; and a seat control system configured to, under control of the processor, move the movable seat such that the surface is exposed.

7. The vehicle of claim 1, further comprising:
an external light control system configured to adjust an amount of external light entering the interior of the vehicle prior to activation of the non-lidar light source.

8. The vehicle of claim 7, wherein the external light control system comprises automatic curtains, automatic shades, automatic louvres, automatic visors, electrochromic elements, an automatic garage door controller, or an autonomous driving system configured to drive the vehicle to a location with a desirable lighting condition.

9. The vehicle of claim 1, wherein the passenger survey system is further configured to receive a second input from the passenger regarding a wear defect of the surface, and wherein the processor is configured, via the non-lidar light source and sensor, to update the stored image of the surface to include the wear defect.

10. The vehicle of claim 1, wherein:
the non-lidar light source comprises an ultraviolet (UV) light source, and the sensor comprises a UV, visible light, or infrared (IR) sensor;
the non-lidar light source comprises a visible light source, and the sensor comprises a visible light camera; or
the non-lidar light source comprises an infrared light source, and the sensor comprises an infrared sensor.

11. A method for cleaning an interior surface of a vehicle, the method comprising:
in a vehicle comprising an interior and an exterior, providing a surface disposed within the interior; and
under control of a processor:
illuminate the surface with a non-lidar light source, wherein the non-lidar light source comprises a blue light source, a violet light source, a near-infrared light source, or a near-ultraviolet light source;
capture a baseline image of the surface with a sensor, while the surface is illuminated by the non-lidar light source;
store the baseline image;
define a detection threshold;
with a passenger survey system, receive an input from a passenger regarding cleanliness of the surface,
adjust the detection threshold based on the input;
capture a current image of the surface with a sensor, while the surface is illuminated by the non-lidar light source;
detect foreign material on the surface based on the detection threshold and a comparison between the current image and the stored image; and
after detecting the foreign material on the surface, clean the surface by activating a cleaning element.

12. The method of claim 11, wherein the passenger survey system is disposed within the interior of the vehicle, and wherein the passenger survey system comprises a touchscreen, a voice interface, a gesture interface, or a housing comprising electromechanical buttons.

13. The method of claim 11, further comprising:
under control of the processor, moving a movable seat such that the surface is exposed.

14. The method of claim 11, further comprising adjusting an amount of external light entering the interior of the vehicle prior to activation of the non-lidar light source.

15. The method of claim 14, wherein adjusting the amount of external light entering the interior comprises activating automatic curtains, automatic shades, automatic louvres, automatic visors, electrochromic elements, an automatic garage door controller, or an autonomous driving system configured to drive the vehicle to a location with a desirable lighting condition.

16. The method of claim 11, further comprising:
under control of the processor:
with the passenger survey system, receiving a second input from the passenger regarding a wear defect of the surface; and
with the non-lidar light source and sensor, updating the stored image of the surface to include the wear defect.

17. The method of claim 11, activating the cleaning element comprises turning on the cleaning element for:
a fixed period of time,
a period of time based on the input, or
a period of time based on a property of the detected foreign material.

18. The method of claim 11, wherein the cleaning element is a UV lamp or a cleaning fluid delivery system.

19. The method of claim 11, wherein:
the non-lidar light source comprises an ultraviolet (UV) light source, and the sensor comprises a UV, visible light, or infrared (IR) sensor;
the non-lidar light source comprises a visible light source, and the sensor comprises a visible light camera; or
the non-lidar light source comprises an infrared light source, and the sensor comprises an infrared sensor.

20. A system for cleaning a surface of an interior of a vehicle, the system comprising:
the vehicle, wherein the vehicle comprises an interior and an exterior;
a surface disposed within the interior;
a processor;
a non-lidar light source configured to illuminate the surface, wherein the non-lidar light source comprises a blue light source, a violet light source, a near-infrared light source, or a near-ultraviolet light source;
a sensor configured to, under control of the processor, capture an image of the surface while the surface is illuminated by the non-lidar light source; and
a stored image of the surface;
a cleaning element configured to, when activated by the processor, clean the surface, a detection threshold;
a movable seat;
a seat control system configured to, under control of the processor, move the movable seat such that the surface is exposed;
an external light control system configured to, under control of the processor, adjust an amount of external light entering the interior of the vehicle prior to activation of the non-lidar light source; and
a passenger survey system disposed within the interior of the vehicle and configured to receive an input from a passenger regarding cleanliness of the surface, wherein the processor is configured to adjust the detection threshold based on the input;
wherein the processor is configured to detect foreign material on the surface based on the detection threshold and a comparison between the captured image and the stored image,
wherein the processor is configured to, after detecting the foreign material on the surface, activate the cleaning element.

* * * * *